United States Patent
Diaz-Arias et al.

(10) Patent No.: US 11,324,439 B2
(45) Date of Patent: May 10, 2022

(54) METHODS AND APPARATUS FOR MACHINE LEARNING TO ANALYZE MUSCULO-SKELETAL REHABILITATION FROM IMAGES

(71) Applicant: University of Iowa Research Foundation, Iowa City, IA (US)

(72) Inventors: Alec Diaz-Arias, Columbia, MO (US); Mitchell Messmore, Iowa City, IA (US); Dmitry Shin, Columbia, MO (US); John Rachid, Iowa City, IA (US); Stephen Baek, Charlottesville, VA (US); Jean Robillard, Iowa City, IA (US)

(73) Assignee: UNIVERSITY OF IOWA RESEARCH FOUNDATION, Iowa City, IA (US)

( * ) Notice: Subject to any disclaimer, the term of this patent is extended or adjusted under 35 U.S.C. 154(b) by 0 days.

(21) Appl. No.: 17/473,526

(22) Filed: Sep. 13, 2021

(65) Prior Publication Data
US 2022/0079510 A1  Mar. 17, 2022

Related U.S. Application Data

(60) Provisional application No. 63/202,298, filed on Jun. 4, 2021, provisional application No. 63/077,335, filed on Sep. 11, 2020.

(51) Int. Cl.
*G06K 9/00* (2006.01)
*A61B 5/00* (2006.01)
(Continued)

(52) U.S. Cl.
CPC .............. *A61B 5/45* (2013.01); *G06N 20/20* (2019.01); *G06T 7/70* (2017.01); *G06T 19/20* (2013.01);
(Continued)

(58) Field of Classification Search
CPC .......... G06F 3/017; G06F 3/011; G06F 3/005; G06F 3/0346; G06F 2203/0381;
(Continued)

(56) References Cited

U.S. PATENT DOCUMENTS

| | | | | |
|---|---|---|---|---|
| 2002/0177770 | A1* | 11/2002 | Lang | A61B 5/4514 600/410 |
| 2009/0082701 | A1* | 3/2009 | Zohar | A61B 5/224 600/595 |

(Continued)

OTHER PUBLICATIONS

Mahum, A Novel Hybrid Approach Based on Deep CNN Features to Detect Knee Osteoarthritis, 2021, Sensors, MDPI (Year: 2021).*

(Continued)

*Primary Examiner* — Alex Kok S Liew
(74) *Attorney, Agent, or Firm* — Ballard Spahr LLP

(57) ABSTRACT

A method can include receiving (1) images of at least one subject and (2) at least one total mass value for the at least one subject. The method can further include executing a first machine learning model to identify joints of the at least one subject. The method can further include executing a second machine learning model to determine limbs of the at least one subject based on the joints and the images. The method can further include generating three-dimensional (3D) representations of a skeleton based on the joints and the limbs. The method can further include determining a torque value for each limb, based on at least one of a mass value and a linear acceleration value, or a torque inertia and an angular acceleration value. The method can further include generating a risk assessment report based on at least one torque value being above a predetermined threshold.

24 Claims, 8 Drawing Sheets

(51) Int. Cl.
*G16H 20/30* (2018.01)
*G06T 19/20* (2011.01)
*G06T 7/70* (2017.01)
*G06N 20/20* (2019.01)
*G06V 40/20* (2022.01)

(52) U.S. Cl.
CPC .............. *G06V 40/23* (2022.01); *G16H 20/30* (2018.01); *G06T 2207/20044* (2013.01)

(58) Field of Classification Search
CPC ........ G06F 3/038; G06F 3/167; G06F 3/0304; G06F 40/44; G06F 40/45; G06T 2207/10016; G06T 2207/30196; G06T 2200/04; G06T 17/00; G06T 7/292; G06T 7/586; G06T 7/593; G06T 7/70; G06T 7/75; G06T 15/04
See application file for complete search history.

(56) References Cited

U.S. PATENT DOCUMENTS

| | | |
|---|---|---|
| 2014/0270351 A1 | 9/2014 | Hoof et al. |
| 2016/0101338 A1 | 4/2016 | Daniels et al. |
| 2016/0220438 A1 | 8/2016 | Walsh et al. |
| 2019/0138607 A1* | 5/2019 | Zhang ................ G06K 9/00355 |
| 2020/0222757 A1 | 7/2020 | Yang et al. |

OTHER PUBLICATIONS

International Search Report and Written Opinion dated Dec. 15, 2021, for PCT/US2021/049876 (9 pages).

* cited by examiner

METHODS AND APPARATUS FOR MACHINE LEARNING TO ANALYZE MUSCULO-SKELETAL REHABILITATION FROM IMAGES

RELATED APPLICATIONS

This application is related to Patent Application No. 63/077,335, entitled "Marker-Less System and Method to Reconstruct Body-Posture from Monocular images to Perform Ergonomic Assessment for Risk Mitigation", filed on Sep. 11, 2020, and to Patent Application No. 63/202,298, entitled "System and Method to Access Musculo-Skeletal Rehabilitation Using Non-intrusive Data Gathering", filed on Jun. 4, 2021. The disclosure of the applications identified above are incorporated herein by reference for all purposes.

TECHNICAL FIELD

The present disclosure relates to the field of artificial intelligence and/or machine learning, and particularly to machine learning methods and apparatus for analyzing musculo-skeletal rehabilitation based on images and/or videos collected from a camera.

BACKGROUND

Musculoskeletal disorders affect one in two adults in the United States representing an estimated 126.6 million Americans costing $213 billion in annual treatment. The most prevalent musculoskeletal condition is arthritis, which affects more than 50 million Americans every year, half of them are adults over the age of 65. It is projected that the prevalence of arthritis will affect 25% of the adult population by 2030 representing about 67 million people. In 2011, it was estimated that the annual cost for treatment of and loss of wages to musculoskeletal disorders was over $213 billion or 1.4% of the gross domestic product (GDP). Taking into account all costs for persons with a musculoskeletal disease, including other comorbid conditions, the total aggregate cost of treating these individuals, plus the cost to society in the form of decreased or lost wages (indirect cost), was estimated to be $873.8 billion per year in 2011.

Therefore, the burden of musculoskeletal disorders is significant and affects the lives of so many people in so many ways. To curb the tremendous societal and economic impact associated with musculoskeletal conditions, the United States Bone and Joint Initiative has recommended that in addition to promoting and funding research, the affected population should receive access to evidence-based treatments, better coordination of care between physicians and other health care providers including physical therapists, and proven strategies to prevent future injuries.

Physical therapy treatment prevents/reduces musculoskeletal conditions, is effective in treating musculoskeletal pain, and improves health. But the benefits of physical therapy treatment are lost when people stop exercising, which usually occurs because of short courses of treatment with limited follow-up. Therefore, the reach of physiotherapists should be increased to home environments, and a patient's progress (range of motion, strength, force, endurance), articular dysfunction, and improvement (pain, articular dysfunction, weakness, fatigue, stiffness) should be monitored more closely and more frequently by both the physical therapist and the patient.

Even though the United States physical therapy industry, which includes about 27,400 rehabilitative therapy practices, had an estimated $38.3 billion in revenue in 2020 and projects annual growth of about 3% per year for the next five years, one of the barriers to deliver physical therapy care to a large number of people and at affordable costs continues to be the paucity of physical therapists relative to population needs, the cost to the patient, and the inability to follow patient progress continuously. Thus, a need exists for improved methods and apparatus for physical therapies.

SUMMARY

In some embodiments, a method includes receiving (1) images of at least one subject and (2) at least one total mass value for the at least one subject. The method further includes executing a first machine learning model to identify joints of the at least one subject. The method further includes executing a second machine learning model to determine limbs of the at least one subject based on the joints and the images. The method further includes generating three-dimensional (3D) representations of a skeleton based on the joints and the limbs. The method can further include determining a torque value for each limb, based on at least one of a mass value and a linear acceleration value, or a torque inertia and an angular acceleration value. The method further includes generating a risk assessment report based on at least one torque value being above a predetermined threshold.

DETAILED DESCRIPTION

Figure 1:
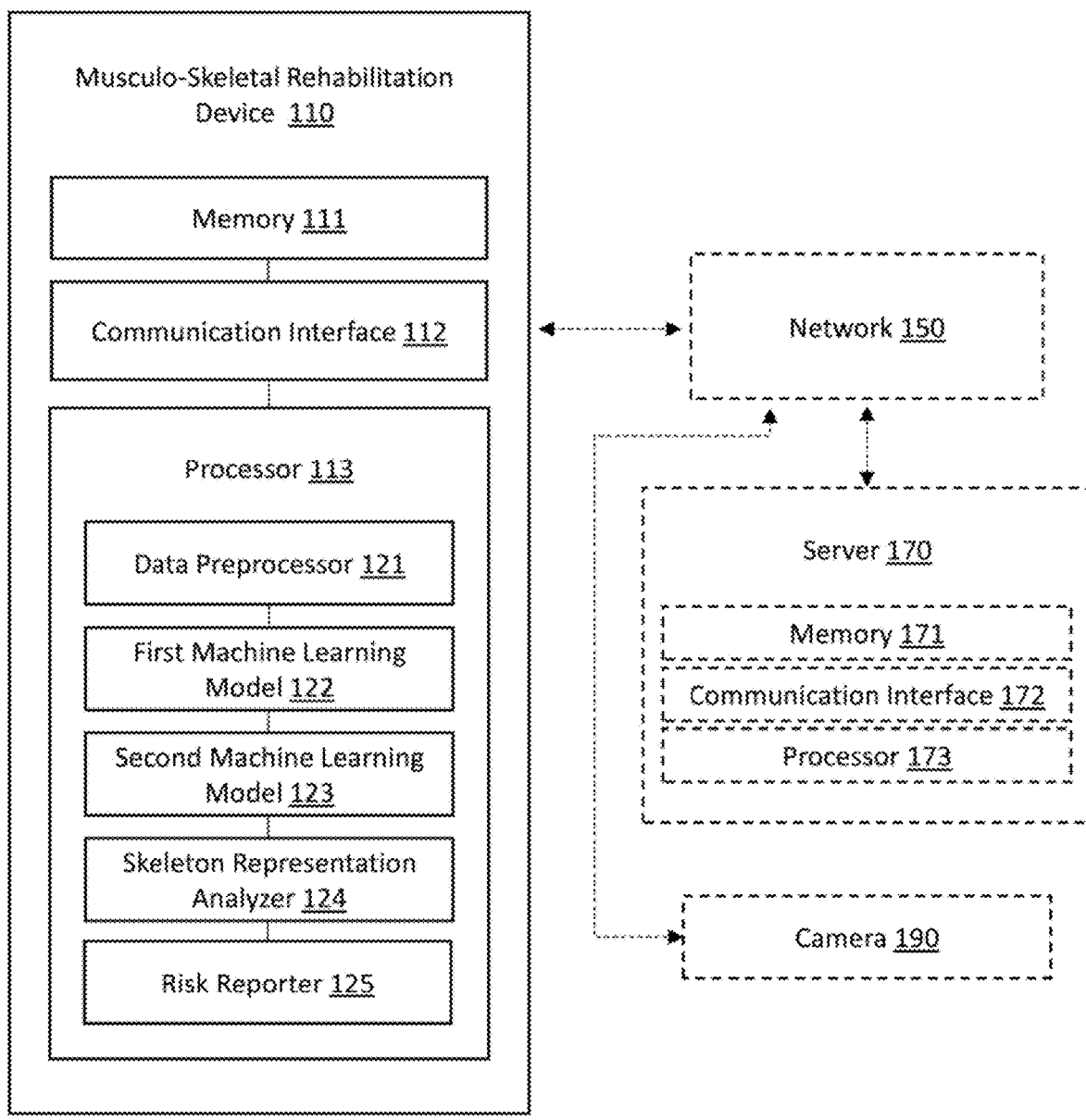
FIG. 1 is a block diagram of a musculo-skeletal rehabilitation device, according to an embodiment.

Non-limiting examples of various aspects and variations of the embodiments are described herein and illustrated in the accompanying drawings.

A lack of timely and accurate feedback and real-time supervision by a healthcare professional is often cited as the most influential factors explaining the slower improvement and patient loss of motivation and engagement during physiotherapy. Furthermore, physical therapy evaluations are often performed intermittently between appointments; these evaluations can be subjective, time-consuming, and can be varied between therapists. To improve an effectiveness of physiotherapy, some known devices and methods have used telerehabilitation, telehealth, video game based-exercise, robotic assistive devices, exoskeletons, haptic devices and/or of wearable devices with limited success. The aging of the population, the growing interest in physical activities, and the broader focus on controlling health care costs to mention a few have increased the need to develop systems allowing patients to perform exercises at their convenience while being monitored continuously, and have resulted in an increasing demand for physical therapists in the United States.

Some known physical therapy methods and apparatus use goniometers to measure a motion of a single joint angle at a single time and to assess thereafter the patient's progress during therapy. An assessment of a range of motion (ROM) evaluation and the ability to record precisely the improvement or changes in the ROM can help to determine a patient's progress during a physical therapy. Such evaluations can be time-consuming and involve collecting data manually on patient's movement. Therefore, such evaluations can be costly and do not always allow for objective, precise, and accurate patient evaluation during active motions.

Some known physical therapy methods and apparatus have demonstrated that the use of sensor(s) attached to the patient's body and associated with the application of machine learning algorithms could accurately measure changes in joint angles and allow for monitoring and recording of joint angle. Some known physical therapy methods and apparatus for robotic therapy have been developed to guide a patient to perform the exact movement, to process a massive amount of data, and to provide quantified information to the patient and the therapist about incremental progress. These approaches, however, present several limitations. First, the technology to acquire data is often quite expensive. Second, the processing of the data is often complex and slow. Third, the sensors, in addition to being expensive, can often impair the patient's motion. Fourth, robotic therapy systems are not generally designed to be used in the home environment and can also be expensive. Fifth, most rehabilitation sessions are performed in a home-based setting, which demands that the systems used be simple and allow for accurate data recording and rapid transmission of the data for continuous oversight of patient exercises and progress by the physical therapist.

Apparatus and methods described herein are low-cost, do not use wearable/worn sensors, and can use artificial intelligence, computer vision, and machine learning on images captured by a camera to continuously and accurately monitor changes in ROM and forces from multiple joints simultaneously. Therefore, the apparatus and methods described herein can be used either in the clinical environment or at home, negating a need for a physical therapist to perform measurements, and remove potential errors associated with inter-tester reliability or incorrect goniometer placement. In addition, the apparatus and methods described herein can have the advantage of measuring the ROM in substantially real-time (e.g., in less than a second) and changes in muscle strength from multiple joints at the same time and with high accuracy. Furthermore, participants do not have to wear sensors or special pieces of equipment or cloth to use the apparatus and methods described herein.

FIG. 1 is a block diagram of a musculo-skeletal rehabilitation device 110, according to an embodiment. The musculo-skeletal rehabilitation device 110 (also referred to as the "compute device"), includes a memory 111, a communication interface 112, and a processor 113 and can be used to store, analyze, and communicate a set of images (also referred to as the "set of frames"). The musculo-skeletal rehabilitation device 110 can be optionally coupled to a camera 190 and/or a server 170, for example, via a network 150, to receive, transmit, store, and/or process images. The images used by musculo-skeletal rehabilitation device 110 can be captured by the camera 190, stored in the memory 111, and/or received from the server 170. For example, the camera 190 can capture a video of at least one subject (e.g., a user(s), a patient(s), a worker(s), etc.) that is not wearing any motion sensors and during a rehabilitation training exercise. The video can include a set of frames and can be stored in the memory 111 to be analyzed by the musculo-skeletal rehabilitation device 110.

The memory 111 of the musculo-skeletal rehabilitation device 110 can be, for example, a memory buffer, a random access memory (RAM), a read-only memory (ROM), a hard drive, a flash drive, a secure digital (SD) memory card, an external hard drive, an erasable programmable read-only memory (EPROM), an embedded multi-time programmable (MTP) memory, an embedded multi-media card (eMMC), a universal flash storage (UFS) device, and/or the like. The memory 111 can store, for example, video data, image data, fitness data, medical record data, and/or the like. The memory 111 can further store one or more machine learning models, and/or code that includes instructions to cause the processor 113 to execute one or more processes or functions (e.g., a data preprocessor 121, a first machine learning model 122, a second machine learning model 123, a skeleton representation analyzer 124, and/or a risk reporter 125).

The communication interface 112 of the musculo-skeletal rehabilitation device 110 can be a hardware component of the musculo-skeletal rehabilitation device 110 to facilitate data communication between the musculo-skeletal rehabilitation device 110 and external devices (e.g., the camera 190 and/or the server 170). The communication interface 112 is operatively coupled to and used by the processor 113 and/or the memory 111. The communication interface 112 can be, for example, a network interface card (NIC), a Wi-Fi® module, a Bluetooth® module, an optical communication module, and/or any other suitable wired and/or wireless communication interface. The communication interface 112 can be configured to connect the musculo-skeletal rehabilitation device 110 to the network 150. In some instances, the communication interface 112 can facilitate receiving and/or transmitting data (e.g., video data, image data, fitness data, medical record data, and/or the like) via the network 150 from/to the camera 160 and/or the server 170.

The processor 113 can be, for example, a hardware based integrated circuit (IC) or any other suitable processing device configured to run or execute a set of instructions or a set of codes. For example, the processor 113 can include a general purpose processor, a central processing unit (CPU), an accelerated processing unit (APU), an application specific integrated circuit (ASIC), a field programmable gate array (FPGA), a programmable logic array (PLA), a complex programmable logic device (CPLD), a programmable logic controller (PLC), a graphics processing unit (GPU), a neural network processor (NNP), and/or the like. The processor 113 can be operatively coupled to the memory 111 and/or communication interface 112 through a system bus (for example, address bus, data bus, and/or control bus; not shown). The processor 113 includes the data preprocessor 121, the first machine learning model 122, the second machine learning model 123, the skeleton representation analyzer 124, and the risk reporter 125. In some implementations, each of the data preprocessor 121, the first machine learning model 122, the second machine learning model 123, the skeleton representation analyzer 124, and/or the risk reporter 125 can include a set of instructions performed by the processor 113 (and/or stored at memory 111, as discussed above). In some implementations, each of the data preprocessor 121, the first machine learning model 122, the second machine learning model 123, the skeleton representation analyzer 124, and/or the risk reporter 125 can include one or more integrated circuits (ICs) in the processor 113 that perform the set of instructions.

The data preprocessor 121 can receive data including video data, image data, fitness data, medical record data, and/or the like, from the camera 190, the memory 111, and/or the server 170. For example, in some instances, the data preprocessor can receive a video (including a set frames; also referred to as the "set of images") of a subject(s) from the camera and an indication of a total mass value(s) of the subject(s). The data preprocessor 121 can be configured, for example, to select data, organize data, and normalize data. In one example, the data preprocessor 121 can associate a first data type from the data with a second data type from the data, for example, to generate a training dataset for training the first machine learning model and/or the second machine ermining model. The first data type can be/include, for example, an image data type, a video data type, etc., and the second data type can be coordinate values representing joints, vectors representing limbs, and/or the like. In some implementations, the association of the first data type and the second data type can be done, for example, by concatenating each datum from a first data type to a datum of a second data type. In one example, the data preprocessor 121 can normalize the set of images to have the same or similar image format, image size, brightness level, contrast level, and/or the like.

The first machine learning model 122 can include a first set of model parameters (e.g., nodes, weights, biases, etc.) so that once the first machine learning model 122 is trained, it can be executed to identify a set of joints of the subject(s) from the set of images. The first machine learning model 122 can be/include, for example, a convolutional neural network (CNN), a graph neural network (GNN), an adversarial network model, an instance-based training model, a transformer neural network, an ensemble of decision trees, an extreme gradient boosting (XGBoost) model, a random forest model, a feed-forward machine learning model, an ensemble of machine learning models, and/or the like.

In one example, the first machine learning model 122 can be a convolutional neural network that includes an input layer, an output layer, and multiple hidden layers (e.g., 5 layers, 10 layers, 20 layers, 50 layers, 100 layers, 200 layers, etc.). The multiple hidden layers can include normalization layers, fully connected layers, activation layers, convolutional layers, downsampling layers, pooling layers, and/or any other layers that are suitable for representing a correlation between images of subjects (e.g., patients, individuals in rehabilitation, etc.) performing rehabilitation exercises, and a representation of joints of the subjects (e.g., coordinates and dimensions of joints of a patient that can be overlaid on an image(s) of the patient).

The second machine learning model 123 can include a second set of model parameters (e.g., nodes, weights, biases, etc.) that can be used to determine a set of limbs of the subject(s) based on the set of joints and the set of images. A set of three-dimensional (3D) representations of a skeleton can be generated based on the set of joints and the set of limbs, as described in further detail herein. The second machine learning model 122 can be/include, for example, a convolutional neural network (CNN), a graph neural network (GNN), an adversarial network model, an instance-based training model, a transformer neural network, an ensemble of decision trees, an extreme gradient boosting (XGBoost) model, a random forest model, a feed-forward machine learning model, an ensemble of machine learning models, and/or the like.

The skeleton representation analyzer 124 can perform numerical differentiation on the set of 3D representations of the skeleton of the at least one subject to produce a linear acceleration value and an angular acceleration value for each limb from the set of limbs of the at least one subject. The skeleton representation analyzer 124 can determine a mass value and a torque inertia value for each limb from the set of limbs, based on the at least one total mass value for the at least one subject and the 3D representation of the skeleton. The skeleton representation analyzer 124 can further determine a set of torque values from the set of limbs, based on at least one of the mass value and the linear acceleration value, or the torque inertia and the angular acceleration value.

The risk reporter 125 can generate a risk assessment report based on at least one torque value from the set of torque values, being above a predetermined threshold. In some instances, a set of predetermined global thresholds can be assigned for the set of joints and stored (e.g., in a look-up table) in the memory 111 of the musculo-skeletal rehabilitation device 110. In some instances, the musculo-skeletal rehabilitation device 110 can be configured to determine an upper bound safe level for the set of joints. For example, in some instances, a Total Limit Value (TLV) of a joint torque can be obtained by a relationship between an allowable percentage of maximum torque on a joint and a duration of the subject performing task. A joint torque above the TLV of the joint torque can lead to fatigue. The subject can be performing a repetitive task such as, for example, a repetitive rehabilitation training exercise for rehabilitation, a repetitive operation of a machinery (e.g., at a factory), and/or the like. The repetitive task, performed by the at least one subject, can have a duty cycle that can be defined as a typical time or an average time it takes the at least one subject to perform one act of the repetitive task or exercise. In one example, the at least one subject can take 20 seconds to perform one cycle (duty cycle) of a repetitive rehabilitation training exercise. At each moment in the subject's duty cycle of performing a task or exercise, a percentage of allowable max torque can be calculated, by the following equation:

$$\% \text{ Allowable Max Torque} = -0.143 \ln\left(\frac{\text{length duty cycle}}{100}\right) + 0.066$$

The percentage of allowable max torque can be multiplied by the TLV of the joint torque to obtain an upper bound for safe/allowable torque on the joint in question.

The camera 190 can be/include a video capturing camera and/or an image capturing camera. The camera 190 can optionally include a memory (not shown), a communication interface (not shown), and a processor (not shown) that are structurally and/or functionally similar to the memory 111, the communication interface 112, and/or the processor 113 as shown and described with respect to the musculo-skeletal rehabilitation device 110. The camera 190 can be operatively coupled to the musculo-skeletal rehabilitation device 110 and/or the server 170 via the network 150. In one example, the camera 190 can be operatively coupled to the musculo-skeletal rehabilitation device 110 via a secured Wi-Fi™ network of a rehabilitation facility. The camera 190 can record images of a subject(s) (e.g., a user(s), a patient(s), etc.) and send the images of the subject(s) to the musculo-skeletal rehabilitation device 110 via the secured Wi-Fi™ network of the rehabilitation facility.

The server 170 can be/include one or more compute devices particularly suitable for data storage, data processing, and/or data communication. For example, the server 170 can include a network of electronic memories, a network of magnetic memories, a server(s), a blade server(s), a storage area network(s), a network attached storage(s), deep learning computing servers, deep learning storage servers, and/or the like. The server 170 can include a memory 171, a communication interface 172 and/or a processor 173 that are structurally and/or functionally similar to the memory 111, the communication interface 112, and/or the processor 113 as shown and described with respect to the musculo-skeletal rehabilitation device 110. The memory 171 can store images, the processor 173 can analyze the images (e.g., crop, normalize, identify joints, determine torque, etc.), and the communication interface 172 can receive/transmit the data from/to the musculo-skeletal rehabilitation device 110 and/or the camera 190 via the network 150.

In use, the data preprocessor 111 can receive a set of images (e.g., a time-sequence of video frames of a video stream) from the camera 190, the memory 111, and/or the server 170. The data preprocessor 111 can prepare the set of images (e.g., normalize the set of images to 256 pixels by 256 pixels image size) for further processing by the musculo-skeletal rehabilitation device 110. In some implementations, the musculo-skeletal rehabilitation device 110 can use a person detector model (can be also referred to as the "third machine learning model"; not shown) to determining a location(s), in each image from the set of images, where a subject(s_(e.g., a patient(s)) is present, and can subsequently classify the subject(s). The person detector model can be/include a convolutional neural network model and be configured to solve a single regression problem. The independent variables of the single regression problem (input of the person detector model) can be the set of images (each including a set of subjects), and the dependent variable of the single regression problem (output of the person detector model) can be bounding box coordinates (e.g., represented by a 4-tuple b=(x,y,w,h)) around the subject(s) and/or probability values for bounding box coordinates. The probability values can indicate probability values that the bounding boxes surround images of a human (e.g., a patient).

In some instances, the bounding boxes can be anchor boxes that predefine a fixed aspect ratio(s) and/or a fixed scale(s) to simplify the person detector model. In some instances, using anchor boxes can reduce a number of possible combinations of bounding box dimensions. In one example, five anchor box aspect ratios can be selected based on a distribution of bounding box instances observed in a training dataset used for training the person detector model. For the person detector model, each location in a $H_i \times W_i$ grid can produce five bounding box instances. The person detector model can be configured such that for each bounding box from the five bounding box instances, a bounding box offset $\Delta b = (\Delta x, \Delta y, \Delta w, \Delta h)$ and a probability that a detected features in an image is a person can also be generated. For example, a generalized backbone feature extractor (e.g., a neck network) can be implemented, subsequent to the person detector model, to generate the bounding box offsets relative to the anchor boxes.

Output of the person detector model is a set of bounding boxes detected for each image from the set of images and is agnostic to one or more adjacent images (e.g., a time-sequence of video frame(s) before and/or after that image). In some implementations, the musculo-skeletal rehabilitation device 110 can use a tracking model (not shown) to identify at least one subject across the set of images. The tracking model can initialize a set of trackers in the first image being earlier in time than each remaining image from the set of images. The tracking model can the use a Kalman filter (or Kalman filter variant) to predict an occurrence of the set of trackers in a subsequent image(s) from the set of images. Given the set bounding boxes predicted from the person detector model and the Kalman filter, an optimal assignment problem can be solved such that the set of trackers across the set of images are matched with the set bounding boxes generated from the set of images. Furthermore, each tracker from the set of trackers can be configured to include or be associated with an appearance model. The appearance model can encode visual information from the set of images into a feature vector. The feature vector can then be used to help solve the assignment problem, by generating additional trackers and/or merging existing trackers based on distances between the set of trackers of the tracking model and the set of bounding boxes generated by the person detector model.

The first machine learning model 122 can then be executed to identify a set of joints of the at least one subject from the set of images. In some instances, for example, the first machine learning model 122 can be a deep fully convolutional neural network (e.g., a deep neural network including 10 convolutional layers, 20 convolutional layers, 100 convolutional layers, 200 convolutional layers, and/or the like). The generalized backbone feature extractor used previously subsequent to the person detector model, described above to generate the set of bounding boxes, can be used in the detection network to generate a multi-scale feature map F. The feature map F can be then fed into a three-stage iterative network to generate part affinity fields (PAFs) $P_i$ (where i=1, 2, or 3). PAFs represent pairwise relationships between body parts in the set of images. After each stage from the three-stage iterative network, the feature map F can be concatenated with previous part affinity field prediction to produce heatmaps. In some instances, the first machine learning model 122 can include convolutional neural networks layers such as, for example, a 7×7 convolutional layer(s) followed by parametric Rectified Linear Unit (PReLU) activation functions to reduce/avoid vanishing gradients and gradient saturation. In addition, in some instances, the first machine learning model 122 can also use skip connections to improve gradient flow.

The second machine learning model 123 can then be executed to determine a set of limbs of the at least one subject based on the set of joints and the set of images. To compose a skeleton(s) from the set of joints detected in the set of images, second machine learning model 123 can use part affinity fields (PAFs). Given two joint types that are to be connected by a body segment, the second machine learning model 123 can compare all possible connections against the PAFs associated with the body segment in the set of images. In one example, $\{J_k\}$, $\{k\ 1, 2, \ldots n\}$ can be two-dimensional (2D) joint locations of the first joint type and $\{R_s\}\{s=1, 2, \ldots m\}$ can be 2D joint locations of the second joint type. For each k and s, integrating a dot product of the PAFs against the unit vector pointing from $J_k$ to $R_s$ over the line segment from $J_k$ to $R_s$ can yield a matching score for the joint pair (limbs). Assigning a score to each joint pair can yield a weighted bipartite graph calculated by:

$$S_{J_k,R_s} := \oint_L P \cdot U_{J_k,R_s}$$

where P is the PAFs from J joints to R joints, L is the line segment between $J_k$ and $R_s$, and $U_{J_k,R_s}$ is the unit vector pointing from $J_k$ to $R_s$. A Hungarian maximum matching algorithm can be applied to optimize/improve matchings between joints (J joints to R joints). Running the PAFs and the Hungarian maximum matching algorithm over all joint connections can produce a set of 2D representations of a skeleton from the set of images.

In some implementations, the set of 2D representations of the skeleton are generated for a time sequence of images (e.g., a video that includes frames/images ordered relative to time). Therefore, jitter or slight differences can exist between consecutive images/frames, which can manifest as noise in a waveform graph of the set of joints. To reduce the jitter, a filter(s) (e.g., signal processing filter) can be used to remove unwanted components of the signal (e.g., remove unwanted measurement noise). For example, a Butterworth filter, which has a frequency response as flat as possible in the passband, can be used to reduce clean/improve motion related data. A Butterworth filter can have a set of specialized parameters including, for example, a cut-off frequency. To obtain a good/optimal cut-off frequency, in some instances, a Jackson's algorithm can be used. Filter parameters of the Jackson's algorithm can be selected to preserve kinetic properties of the set of 2D representations of the skeleton. To further smooth the data, a final median filter and/or Savgol filter, initialized based on a frame rate of the set of images and/or video, can be applied to the set of 2D representations of the skeleton to obtain a more smooth/continuous 2D pose estimation amongst the set of 2D representations of the skeleton. Furthermore, a Savgol filter can be used to increase a precision of the 2D pose estimation. The Savgol filter can locally fit data using low degree polynomials, which can result in a smooth waveform that can preserves important aspects of the data. In some instances, to generate a more robust 2D pose estimation, the musculo-skeletal rehabilitation device 110 can perform matching by associating a representation of the skeleton from the set of 2D representations of the skeleton to a specific bounding box instance by taking the skeleton with the highest number of joints located in the bounding box.

In some implementations, the set of 2D representations of the skeleton generated using matching of joints and the Hungarian maximum matching algorithm can be tracked from frame to frame of the set of images using the set of trackers given used in the tracking model described above. From a tracked bounding box, the musculo-skeletal rehabilitation device 110 can determine if a skeleton from the set of 2D representations of the skeleton matches with the bounding box by checking if a threshold number of skeletal points reside in the bounding box. If the threshold is met, the skeleton inherits the tracking identification of the bounding box. Additional analysis on the inclusion of a skeleton in a bounding box can be used to prevent/reduce misidentification of skeletons due to a bounding box overlap(s). In some implementations, the musculo-skeletal rehabilitation device 110 can assign an intersection score to pairs of overlapping bounding boxes from the set of bounding boxes to determine a significance of an overlap. Comparing coordinates of the set of 2D representations of the skeleton in pairs with high intersection scores, can improve tracking of skeletons that are contained in multiple bounding boxes from the set of bounding boxes.

The musculo-skeletal rehabilitation device 110 can then generate a set of three-dimensional (3D) representations of a skeleton based on the set of joints and the set of limbs. The musculo-skeletal rehabilitation device 110 can use, for example, a fully convolutional neural network that accepts an input trajectory of a predefined window size(s) and subsequently regresses the 3D skeleton of a middle frame of a time sequence of the set of images. In one example, the fully convolutional neural network can use 2048 3×3 convolution filters and 1×1 convolution filters with batch normalizations following the 3×3 convolution filters. In addition, skip connections can be used to improve a gradient flow during training the fully convolutional neural network. For example, in some instances, a preset window size of 161 images can be used. The fully convolutional neural network can be trained by minimizing:

$$\sum_i \|y_i - f(x_i)\| + \sum_i \|P(y_i) - P(f(x_i))\|$$

where $x_i$ represents an input trajectory, $y_i$ represents the ground truth pose of the middle frame, P denotes the perspective projection and f is the learned mapping. In some instances, augmenting the input with adjacent frame can provide additional context and improve an overall performance of generating these set of representations of the skeleton.

In some implementations, a monocular depth estimation model (also referred to as the "third machine learning model") can be used to encode a distance of an object (e.g., a patient, a load, etc.) relative to a focal center of the camera 190. The monocular depth estimation network can receive an image (e.g., image 810 shown in FIG. 8) from the set of images in red-green-blue (RGB) color coding to generate a monocular image (e.g., image 820 shown in FIG. 8) that is down-sampled by a factor of two. In some instances, the monocular depth estimation network can be an autoencoder. In one example, monocular depth estimation model can use transfer learning from a densely connected convolutional neural network (DenseNet) backbone, include a header network with 3 convolutional layers followed by an upsampling layer to achieve a desired output resolution. The monocular depth estimation model can be trained by minimizing the following loss function:

$$\frac{1}{n}\left(\sum_p |y - f(x)| + \sum_p |\nabla_x(y_p, f(x)_p)| + |\nabla_y(y_p, f(x)_p)|\right)$$

where n represents the number of images in the set of images, y represents the ground truth depth map and f(x) is a predicted depth map from the set of images x. Lastly, $\nabla$ represents the gradient with respect to a variable.

In some implementations, depth information from the monocular depth estimation model can be correlated with z coordinates of the set of joints in a camera reference image to reduce a complexity of the 3D representations of the skeleton (also referred to as the 3D pose estimate) by solving depth ambiguity. In some implementations, the above processes can be performed in a root relative camera space.

3D representations of the skeleton (also referred to as the "first 3D representations of the skeleton") can be represented in a Cartesian coordinate system having (x, y, z) coordinate representation for each joint in the set of joints. The skeleton, however, can also be represented by rotation and translation matrices (also referred to as the "second 3D representations of the skeleton"). At a first joint in the skeleton, a 3D coordinate system is centered at the first joint and a z-axis agreeing with a line segment connecting that joint to a second joint in the skeleton. Because the two joints are connected by a limb in the skeleton, a special Euclidean matrix can transform the first coordinate system to the second coordinate system. The rotation and translation matrices can completely represent the 3D skeleton and further provide joint angle and limb length information. For example, $\{M_j\}$ $\{j=1, 2 \ldots, k\}$, where k is the number of joints in the skeleton, are 3D special Euclidean (SE) matrices. To reconstruct the joint locations using the SE matrices, a root joint matrix $M_1$ can be applied to the origin of a global coordinate system to result in a location of the root joint of the set of joints. Applying the matrix $M_2$ to the root joint can result in the next joint in the skeleton hierarchy. In general, the (J+1)th joint can obtained by applying the product $M_1$ $M_2$ $M_3$ ... $M_J$ to the root joint. The SE matrices can be decomposed into a translation, and three rotations about the x, y, and z coordinate axes respectively. Hence, from the SE matrix representation of the skeleton, a set of joint angles can be easily determined.

The set joint angles of the skeleton can then used to perform musculo-skeletal analysis to generate kinetic parameters including speed, acceleration, torque, and/or the like. Hence, the musculo-skeletal rehabilitation device 110 can include a process to transform 3D cartesian coordinates into an equivalent representation by special Euclidean matrices. This process can be also referred to as the inverse kinematics and does not always have a unique solution. To obtain/select a solution(s), the musculo-skeletal rehabilitation device 110 can perform an iterative optimization process that compares an outcome of inverse kinematics to the back-projected forward kinematics cartesian coordinates. An improved/optimal solution would be one in which a composition map of the inverse kinematics and the back-projected forward kinematics yields the identity map. At each iteration, this solution can improve by minimizing a squared distance between the identity and the composition map.

For example, let FK denote the forward kinematics layer that maps from SE(3) matrix to cartesian coordinate ($R^3$) and let IK denote the inverse kinematics layer mapping $R^3$ to SE(3). For each special Euclidean matrix M, the iterative optimization process looks for the corresponding point x in $R^3$ to minimizes the loss:

$$L(x)=|FK(IK(x))-x|$$

starting with an initial guess for x. At each iteration, the iterative optimization process moves a small distance in the direction of the gradient to find a better approximation for x:

$$x_{new}=x+\in \nabla L(x)$$

$\in$ being small positive number. In practice, computing the gradient of L is not trivial and can be computationally costly. For this reason, a Broyden-Fletcher-Goldfarb-Shannon algorithm can be used for unconstrained nonlinear optimization problems. In short, the algorithm implements a gradient descent method described above, which is further informed by the curvature of the loss surface to reduce the complexity of the algorithm.

The output from the IK layer (the inverse kinematics layer mapping $R^3$ to SE(3)) can produce tuples for each joint from the set of joints as ($\theta_x$, $\theta_y$, $\theta x$) called the Euler-angle representation. The Euler-angle representation can be associated with a rotation matrix R. The rotation matrix R satisfies $RR^t=R^tR=1$, where t represents a transpose operation, and I represents an identity matrix. The space of all 3×3 rotation matrices can be denoted by SO(3) and is called the special orthogonal group. The musculo-skeletal rehabilitation device 110 can include a neural network (with custom layers) that can be trained on an arbitrary product of SO(3)'s on natural 3D human poses and with respect to the Riemannian loss on SO(3)× . . . ×SO(3). The neural network can compress corrupted motion trajectories to a latent space with respect to temporal dimension of the set of images to unravel a true motion(s). The neural network can denoise previously reconstructed motions that may invariably contain a certain amount of noise. In effect, the neural network can learn the space of valid articulable human poses and takes in a possibly invalid pose that has been reconstructed and can project it onto a valid pose.

The time series of Euler-angle representations (also referred to as the "joint posture information"), derived from the IK optimization above and then subsequently smoothed, can be denoted by $\Theta_i(t)$, which represents joint angles θ of movements i as a function of time t. Numerical differentiation can be used to generate a time series of joint movement velocity values from the time series of joint posture information, as follows:

$$v_i(t)=(\theta_i(t-1)-\theta_i(t+1))/(2\times \Delta t)$$

where Δt is the inverse of the video/image recording frame rate. In some cases, the absolute value of $v_i(t)$ can be taken as the time series of the joint movement velocity values.

From $\Theta_i(t)$ a first set of metrics of exposure can be generated, including, but not limited to, a mean joint posture, a 5th, 10th, 50th, 90th, 95th and/or other selected percentiles of a cumulative joint posture distribution, a joint posture range, a difference between the 95th and 5th percentiles, a difference between the 90th and 10th percentiles, a proportion of recorded video in different categories of joint posture, a proportion of recorded video with neutral joint posture, a proportion of recorded video with extreme joint posture, a proportion of recorded video with neutral joint posture for at least three continuous seconds, or a number per minute of periods with neutral posture for at least three continuous seconds. In some instances, the at least one subject (e.g., a patient) can enter joint posture categorization schemes customized to needs. Alternatively, thresholds for 'neutral' and 'extreme' postures can be derived.

From $v_i(t)$, a second set of metrics of exposure can be generated, including, but not limited to, a mean joint movement speed, a 5th, 10th, 50th, 90th, and 95th and/or other selected percentiles of the cumulative joint movement speed distribution, a joint movement speed range, a difference between the 95th and 5th percentiles, a difference between the 90th and 10th percentiles, a proportion of recorded video with low joint movement speed, a proportion of recorded video with high joint movement speed, a proportion of recorded video with low movement speed for at least three continuous seconds, or a number per minute of periods with low movement speed for at least three continuous seconds. Furthermore, using a combination of $\Theta_i(t)$ and $v_i(t)$, a third set of metrics of exposure can be generated, including, but not limited to, a proportion of recorded video with both neutral 5 postures and low velocity, a proportion of recorded video with both neutral posture and low velocity for at least three continuous seconds, and a number per minute of periods with both neutral posture and low velocity for at least three continuous seconds.

Dynamic and static joint torque of the at least one subjects' joints can be calculated using the 3D representations of the skeleton, along with the at least one subject' mass, a mass and location of objects interacting with the at least one subject. In some implementations, the at least one subject's mass and/or the mass of the objects interacting with the at least one subject may be obtained via a peripheral neural network or via user input. Furthermore, the 3D representations of the skeleton can be used to model a maximum torque value on each joint, which can in turn be used to determine a total limiting value at each time in a duty cycle. The total limiting value can provide a useful fatigue indicator, which ergonomists and safety managers can use, for example, to improve workplace safety.

The skeleton representation analyzer 124 of the musculo-skeletal rehabilitation device 110 can determine a load acting on a joint from the set of joints of the 3D representations of the skeleton at a given time. Using load, a set of torque values can be calculated, which can indicate the net result of all muscular, ligament, frictional, gravitational, inertial, and reaction forces acting on the set of joints. To determine/compute a static load on the back joint (e.g., joint L5/S1 shown in FIG. 6) the skeleton representation analyzer 124 can individually compute the torque of inertia of the torso, arms, hands, and handheld object about the back joint using the following equation:

$$torque = L*W + M*A + I*\alpha$$

where L represents a torque arm, W represents a weight of a limb from the set of limbs, M represents a mass of the limb, A represents a linear acceleration value of a center of mass of the limb, I represents a torque inertia, and a represents an angular acceleration value of the limb with respect to the ground plane.

The mass of the limb can be derived from Dempster's equations and a total mass value (e.g., in medical record stored in the memory Ill or the server 170) of the at least one subject (e.g., the patient). In some instances, the at least one subject can directly input the total mass value. In some instances, a neural network model can be used to estimate the total mass value from the set of images. The center of mass (COM) of each body part can be obtained using the 3D representations of the skeleton, along with anatomically derived data. In some instances, a COM of a hand-held object (e.g., used by patient to perform an exercise) can be obtained by (1) executing a neural network to detect the object, and (2) modeling a shape and/or a mass of the hand-held object by comparing it with simpler geometric objects such as a rectangular prism(s), a sphere(s), and/or the like. The linear acceleration value and the angular acceleration value can be computed using a first central difference method. The torques for each segment above a back joint can be calculated and summed to compute a total torque (moment) value.

As described above, the skeleton representation analyzer 124 of the musculo-skeletal rehabilitation device 110 can generate a torque value on each joint of the at least one subject to produce a set of torque values. To contextualize torque data (the set of torque values), the risk reporter 125 can analyze the torque data to indicate when a torque value from the set of torque values is above a safe level (e.g., when the torque is at a level above a previously-determined threshold, risk of fatigue is likely high).

For a given joint from the set of joints, a joint angle can be derived from the 3D representations of the skeleton and using 3D trigonometry. Furthermore, a velocity value of the given joint can be calculated, for example, using the discrete difference method, described above, which can compare a change in joint angle in a frame from a previous frame and a next frame. Therefore, a maximum torque for the joint can be obtained based on the joint angle and the velocity value. The risk reporter 125 can then determine an upper bound safe level for the joint. In one example, a Total Limit Value (TLV) of a joint torque on the joint can be obtained by a relationship between an allowable percentage of maximum torque on a joint and a duration of the subject performing task as described above.

The risk reporter 125 can include a statistical model that can compute and report statistical data including, but not limited to, means and variances of the set of joint angles (derived from the set of joints) and the set of poses (generated from the 3D representations of the skeleton). The statistical model can also be used to conduct various statistical studies such as analysis of variance (ANOVA) of joint movements under different ergonomic interventional guidelines. The outcomes of statistical studies can be incorporated into a dashboard for visualization and analysis to a user (e.g., a physician, a patient, a clinician, etc.) of the musculo-skeletal rehabilitation device 110.

The statistical model of the risk reporter 125 can perform partitioning and hierarchical data clustering such as Gap Statistic-enabled K-Means, Mean-Shift, density-based spatial clustering of applications with noise (DBSCAN), and/or the like. Expectation maximization and agglomerative clustering techniques can be used to identify intrinsic groups of poses occurred during specific exercises and/or manufacturing operations. In some implementations, the data clustering can be performed separately for joint angles/positions, inter-joint distance, as well for combined measurements, which incorporate multi-objective optimization methods. The identified pose groups can then be studied and used in feature engineering for data classification and predictive analytics pipelines. Association Rules and Contrast Mining algorithms such as Apriori, frequent pattern (FP)-growth, and/or the like can be used to uncover inter-relationships among the set of joints in form of high-explanatory rules and contrast sets, which can result in better understanding of the ergonomic risk boundaries in specific organizational settings.

Figure 7:
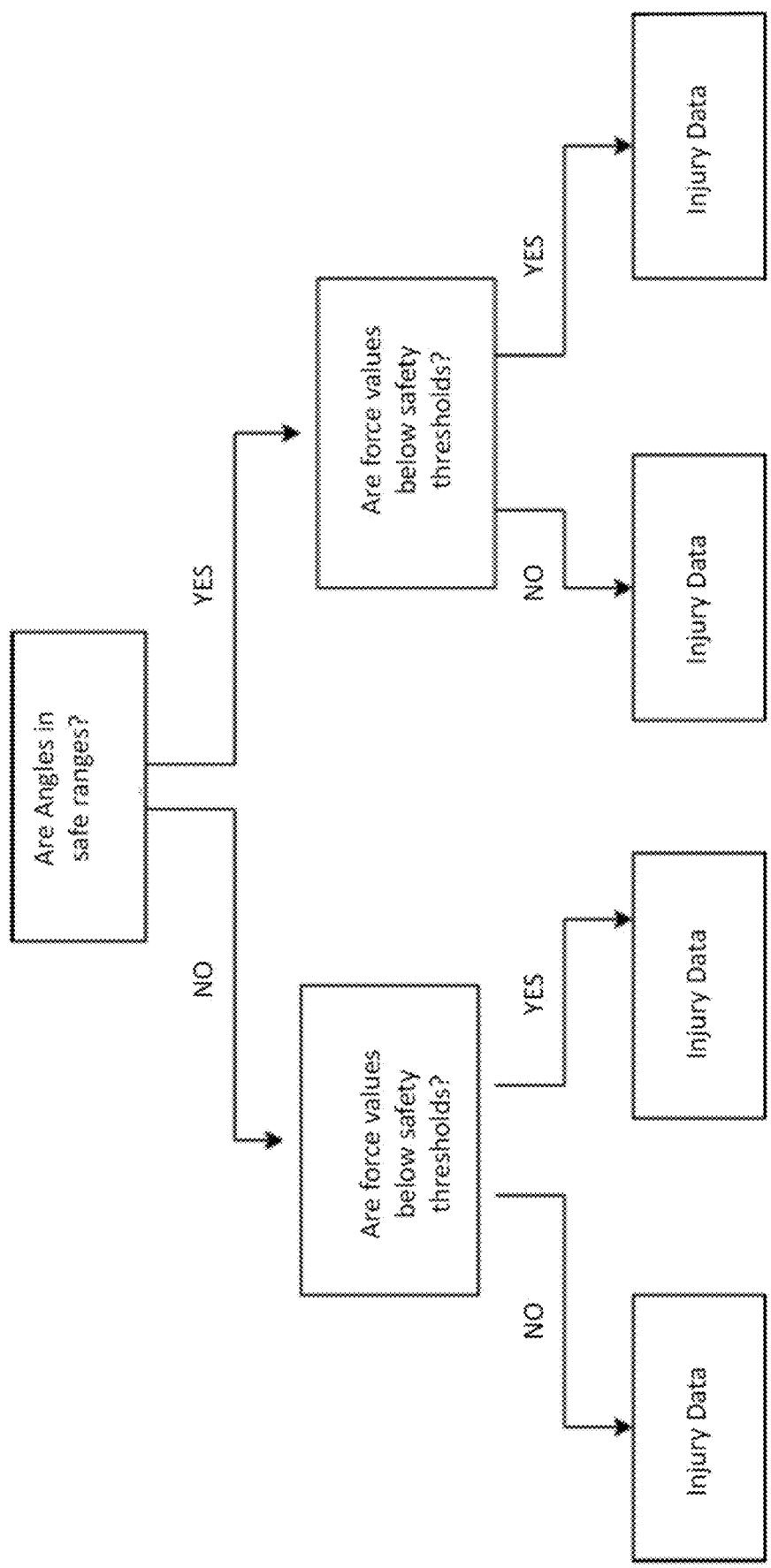
FIG. 7 is a schematic illustration of a classification model for classifying static pose data and dynamic pose data into risk injury categories, according to an embodiment.

The risk reporter 125 can include a classification model (also referred to as the "third machine learning model"; e.g., shown in FIG. 7). The classification model can be/include a gradient boosting decision tree algorithms such as an eXtreme Gradient Boosting (XGBoost) model. In some instances, the XGBoost model can exhibit better performance over non-ensemble-based classification methods. The XGBoost model can classify static pose and/or dynamic pose data into predefined risk injury categories. The classification model can classify the set of poses of the at least one subject to a set of predetermined injury categories to generate a set of likelihood values for occurrence of an injury (ies).

Therefore, the risk reporter 125 can use predictive analysis (using a statistical model(s) and a machine learning model(s)) to establish thresholds on safety measures to prevent increase of risks of injuries. In some instances, Long-Short-Term (LSTM) Recurrent Neural Networks (RNN) as well as Transformer-based machine learning pipelines can be used to exploit time-series data for prediction of adverse effects of specific poses that occurred during manufacturing operations. Classification outcomes can then be visualized in the dashboard for visualization and analysis to a user (e.g., a physician, a patient, a clinician, etc.) of the musculo-skeletal rehabilitation device 110, and/or be used to analyze organization-specific risk factors.

Although the musculo-skeletal rehabilitation device 110, the server 170, and the camera 190 are shown and described with respect to FIG. 1 as singular devices, it should be understood that in some embodiments, one or more musculo-skeletal rehabilitation devices, one or more servers, and/or one or more cameras can be used. For example, in some embodiments, multiple cameras (not shown) can be used to capture the set of images of the subject(s). Each camera can be installed at a different position in the room to capture a perspective different from the remaining cameras from the multiple cameras.

In some embodiments, the musculo-skeletal rehabilitation device 110 can include the camera 190. For example, the camera can be part of the musculo-skeletal rehabilitation device 110 (e.g., a webcam connected to the musculo-skeletal rehabilitation device 110, a camera integrated into the musculo-skeletal rehabilitation device 110) and can be operatively coupled to the memory 111, the communication interface 112, and/or the processor 113 to store, transmit, and/or process the set of images captured by the camera. In some instances, the camera 190 can include multiple frame rate settings and the processor 113 can be configured to determine a frame rate from the multiple frame rate settings, based on a memory storage available in the memory 112 of the musculo-skeletal rehabilitation device 110 and/or in the memory 171 of the server 170. In some embodiments, the camera 190 can be directly connected to the musculo-skeletal rehabilitation device 110. That is the camera 190 does not use the network 150 to connect to the musculo-skeletal rehabilitation device 110.

Figure 2:
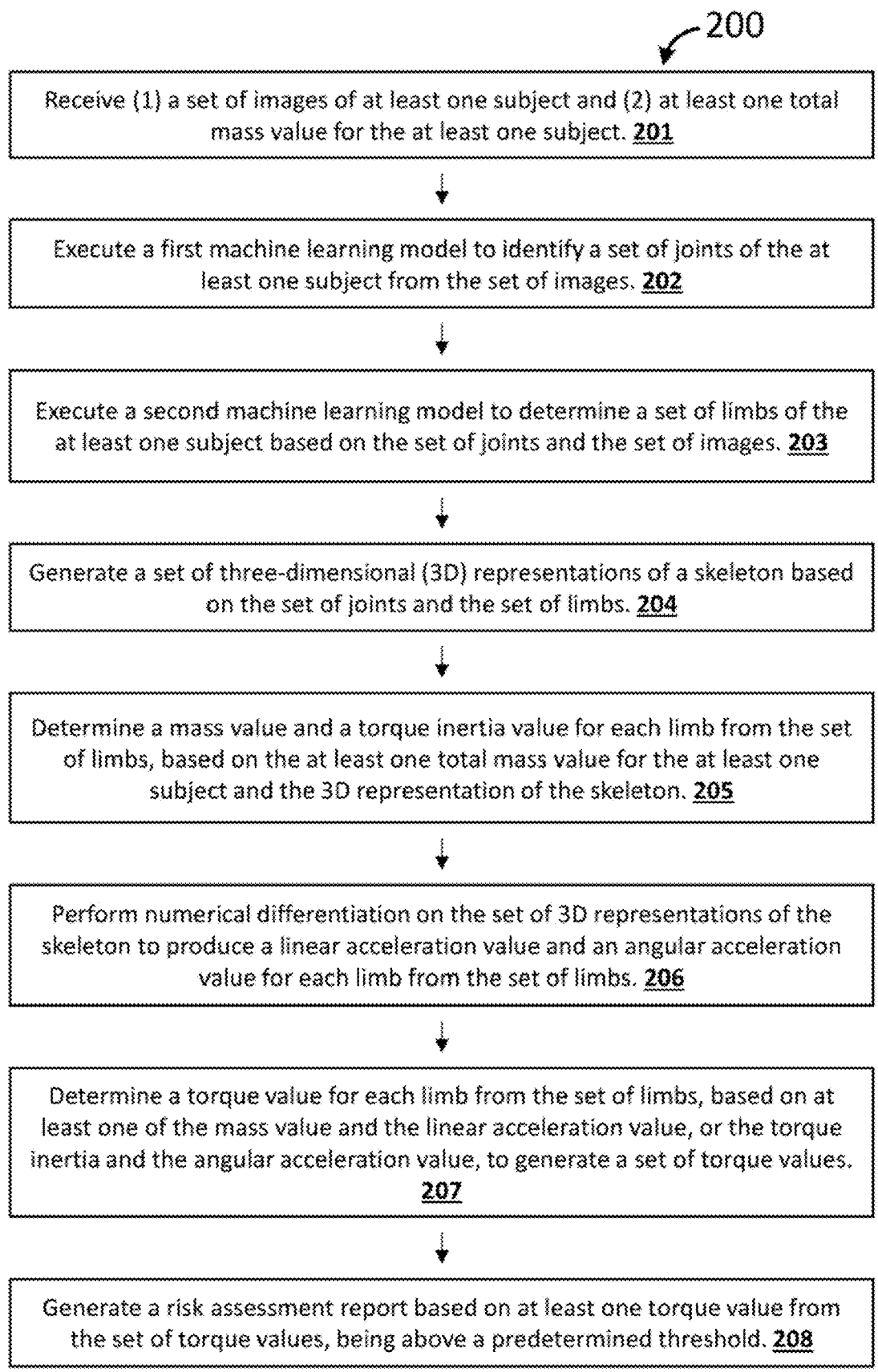
FIG. 2 is a flowchart showing a method for analyzing musculo-skeletal rehabilitation from a set of images, according to an embodiment.

FIG. 2 is a flowchart showing a method 200 for analyzing musculo-skeletal rehabilitation from a set of images, according to an embodiment. As shown in FIG. 2, the method 200 can be performed by a musculo-skeletal rehabilitation device (e.g., the musculo-skeletal rehabilitation device 110 as shown and described with respect to FIG. 1). At 201, (1) a set of images of at least one subject and (2) at least one total mass value for the at least one subject can be received. The at least one subject is not wearing any motion sensors. In some instances, the set of images can be ordered in a time sequence (e.g., time sequence of a set of frames in a video stream). In some implementations, a person detector model (described with respect to FIG. 1; also referred to the "third machine learning model") can be executed to generate a set of bounding boxes around the at least one subject in the set of images.

In some implementations, a set of trackers (e.g., one or more image markers that can be easily identified in an image) can be placed in a bounding box of a first image (earlier in time than each remaining image from the set of images) in the time sequence of the set of images. In some implementations, the musculo-skeletal rehabilitation device can execute a Kalman filter (e.g., a variation of Kalman filter) to track the set of trackers to identify the at least one subject across the set of images.

At 202, a first machine learning model (similar to the first machine learning model 122 shown and described with respect to FIG. 1) can be executed to identify a set of joints of the at least one subject from the set of images. At 203, a second machine learning model (similar to the second machine learning model 123 shown and described with respect to FIG. 1) can be executed to determine a set of limbs of the at least one subject based on the set of joints and the set of images. In some implementations, the musculo-skeletal rehabilitation device can execute a Hungarian maximum matching algorithm to determine a set of relationships between the set of joints at each image from the set of images. The set of joints and the set of relationships can be used to produce at least one skeleton for the at least one subject.

At 204, a set of three-dimensional (3D) representations of a skeleton can be generated based on the set of joints and the set of limbs. In some implementations, the musculo-skeletal rehabilitation device can apply at least one filter (e.g., a Butterworth filter, a final median filter, a Savgol filter, and/or the like) to the set of 3D representations of the skeleton to generate at least one pose. The at least one filter can be determined based on a frame rate (e.g., a frame rate of the camera 190 as shown and described with respect to FIG. 1) used for recording/capturing the set of images. In some implementations, the musculo-skeletal rehabilitation device can denoise the set of 3D representations of the skeleton based on the at least one pose to produce a set of refined (e.g., with less noise) 3D representations of the skeleton.

In some implementations, the musculo-skeletal rehabilitation device can execute, after executing the second machine learning model, a monocular depth estimation model (also referred to as the "third machine learning model"; e.g., an autoencoder neural network model) to generate at least one distance, relative to a focal point of the camera, based on the set of images of the at least one subject. At least one pose can be generated based on the at least one distance and the set of 3D representations of the skeleton. The set of 3D representations of the skeleton can be denoised based on the at least one pose to produce a set of refined (e.g., with less noise) 3D representations of the skeleton.

At 205, a mass value and a torque inertia value can be determined for each limb from the set of limbs, based on the at least one total mass value for the at least one subject and the 3D representation of the skeleton. In some implementations, the mass value can be generated by a peripheral neural network or via a user input. At 206, a numerical differentiation on the set of 3D representations of the skeleton can be performed to produce a linear acceleration value and an angular acceleration value for each limb from the set of limbs. The total mass of the at least one subject may be provided by the user or can be estimated using a 3D representation of a skeleton in conjunction with an auxiliary neural network that can predict the Body Mass Index (BMI) of the at least one subject. In some implementations, facial features, which are highly correlated with BMI, can be used to predict the BMI of the at least one subject and/or total mass. For example, a convolutional neural network (CNN) can be trained to take in facial images from a sub-collection of frames of the video capture. The facial features can be extracted via feature maps and the network can use those features to directly regress the BMI of the at least one subject. A height of the at least one subject can be extracted from the 3D representation of the skeleton. The height and BMI together can be used to obtain the subject's weight.

At 207, a torque value for each limb from the set of limbs can be determined, based on at least one of (1) the mass value and the linear acceleration value, or (2) the torque inertia and the angular acceleration value, to generate a set of torque values. In some implementations, the torque value can be determined for each limb from the set of limbs, based on a weight value a torque arm value, the mass value, the linear acceleration value, the torque inertia, and the angular acceleration value. At 208, a risk assessment report can be generated based on at least one torque value from the set of torque values, being above a predetermined threshold. In some implementations, the 3D representations of the skeleton can be Cartesian coordinate matrices and be referred to as a first set of 3D representation of the skeleton. The first set of 3D representation of the skeleton can be transformed, using at least one Euclidean matrix, to produce a second set of 3D representations (Euler-angle representations) of the skeleton. A numerical differentiation can be performed on the second set of 3D representations of the skeleton to produce a set of time sequences of joint movement velocity values.

Figure 3:
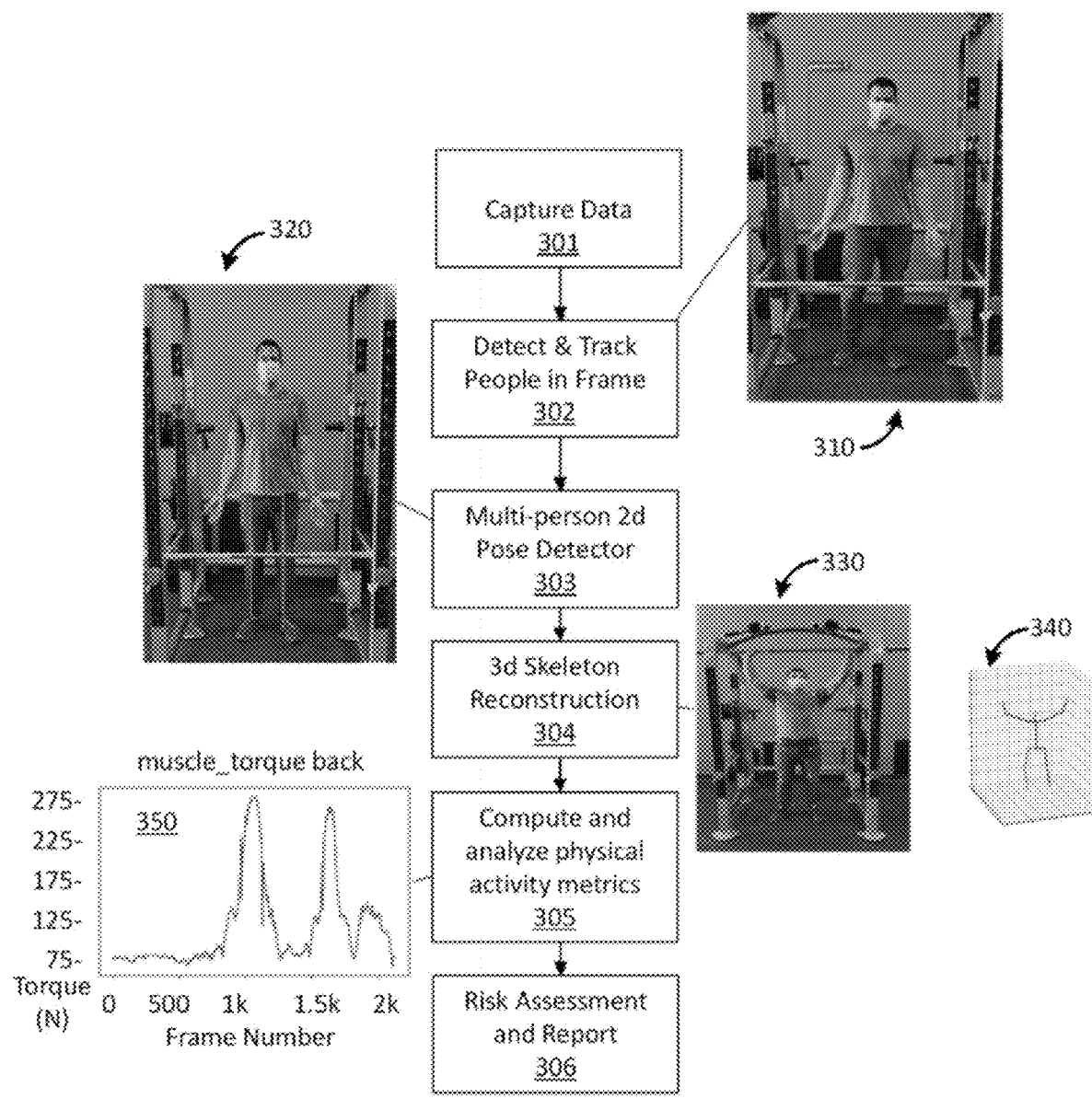
FIG. 3 is a schematic illustration of a method for analyzing musculo-skeletal rehabilitation of a subject from a set of images, according to an embodiment.

FIG. 3 is a schematic illustration of a method for analyzing musculo-skeletal rehabilitation of a subject from a set of images, according to an embodiment. In some embodiments, the method can be performed by a musculo-skeletal rehabilitation device (e.g., the musculo-skeletal rehabilitation device 110 as shown and described with respect to FIG. 1). At 301, data can be captured. The data can include a set of images of a subject (e.g., an individual performing a physical exercise), an indication of weight of the subject, and/or the like. At 302, a bounding box can be generated (e.g., by a person detection model described with respect to FIG. 1) around the subject to produce an image annotated with the bounding box 310. (Although not shown in 310, it should be understood that each full image is larger than and excluded from the bounding box.) In some implementations, the bounding box can be used to track the subject, as described above. At 303, a 2D pose can be generated for each image from the set of images of the subject using a multi-person 2D pose detector model, as described above. The 2D pose can be overlaid with the image to produce an image annotated with the 2D pose 320. At 304, a 3D pose can be generated for an image using a 3D skeleton reconstruction model, as described above. The 3D pose can be overlaid with the image to produce an image annotated with the 3D pose 330. In addition, a 3D representation of a skeleton 340 of the subject can be produced by the 3D skeleton reconstruction model. At 305, the 3D representation of the skeleton 340 can be used to compute and analyze physical activity metric (e.g., velocity values, torque values, etc.), as described above. For example, in some instances, a time sequence of torque value in units of Newton (N) can be analyzed and/or plotted for visualization to a user of the musculo-skeletal rehabilitation device. At 306, all or some of the physical activity metrics can be used to produce a risk assessment report. In some instances, the risk assessment report can specifically indicate a likelihood of a particular joint being at risk of injury and/or fatigue.

Figure 4:
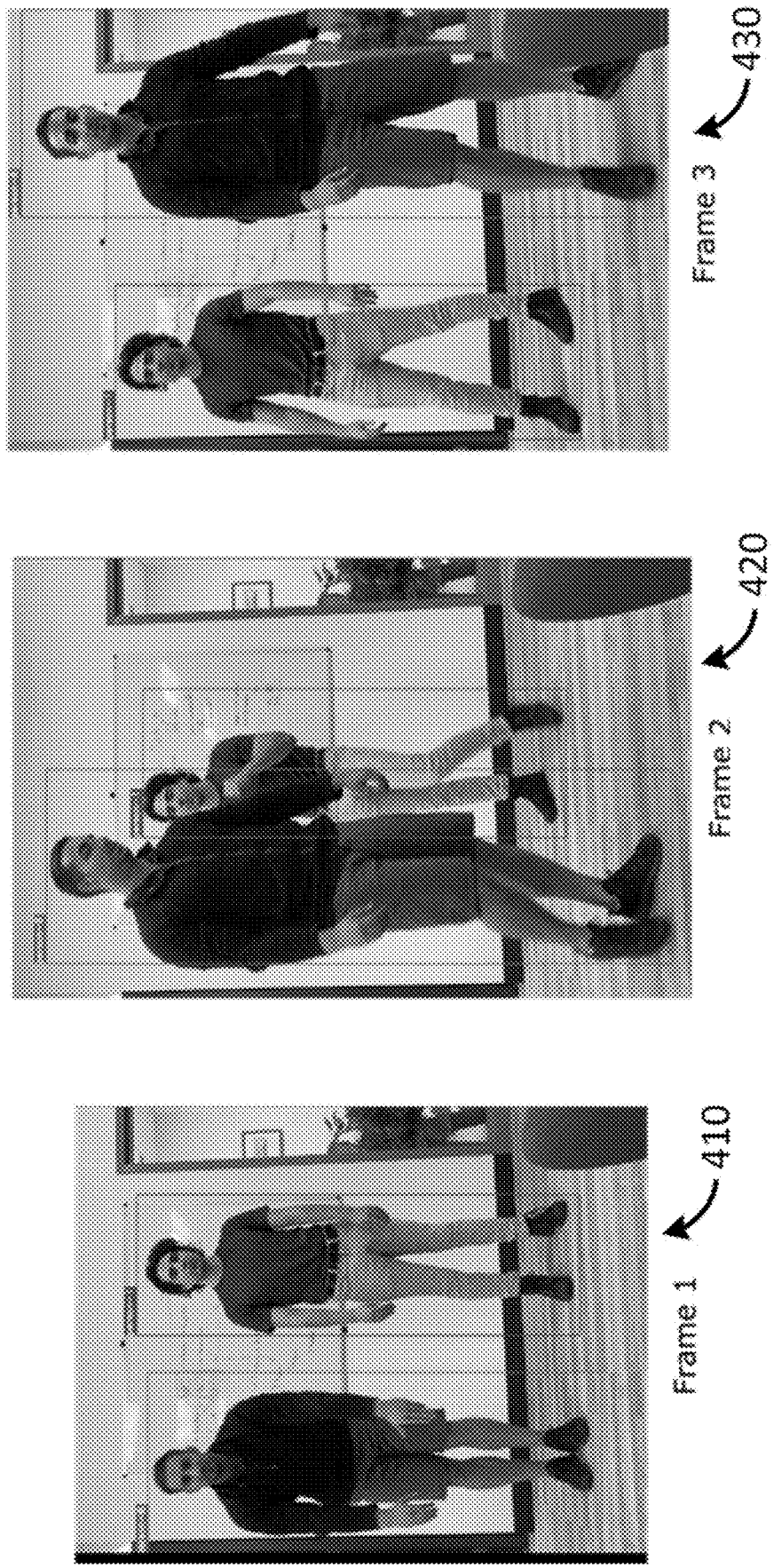
FIG. 4 is a schematic illustration of a method for detecting a set of subjects and tracking the set of subject across frames, according to an embodiment.

FIG. 4 is a schematic illustration of a method for detecting a set of subjects and tracking the set of subjects across frames, according to an embodiment. A musculo-skeletal rehabilitation device (similar to the musculo-skeletal rehabilitation device 110 described with respect to FIG. 1) can generate multiple bounding boxes and multiple representations of skeletons for multiple subjects in a set of images (e.g., video frames). A tracking model (similar to the tracking model described above with respect to FIG. 1) can track the multiple bounding boxes and the multiple representations of skeletons across frames of the set of images, using a set of trackers used in the tracking model described above.

Figure 5:
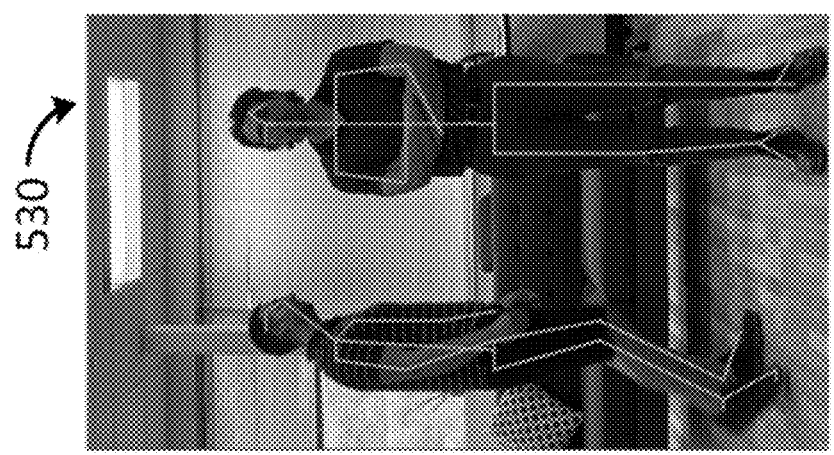
FIG. 5 is a schematic illustration of a method for estimating a set of poses, according to an embodiment.
Figure 5:
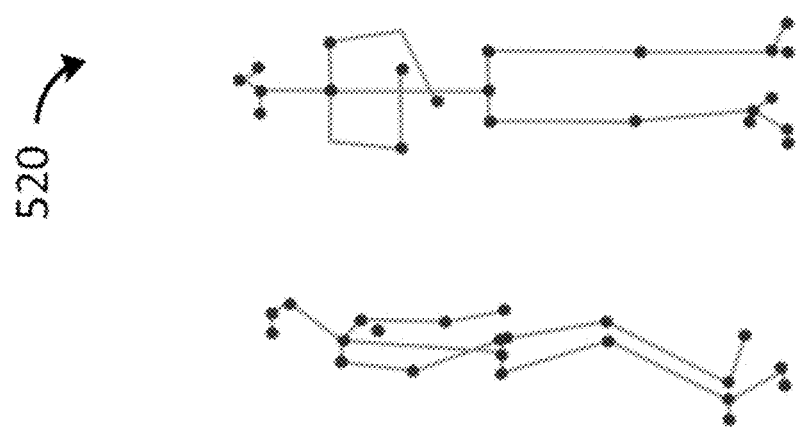
Figure 5:

FIG. 5 is a schematic illustration of a method for estimating a set of poses, according to an embodiment. A musculo-skeletal rehabilitation device (similar to the musculo-skeletal rehabilitation device 110 described with respect to FIG. 1) can use the first machine learning model (similar to the first machine learning model 122 shown and described with respect to FIG. 1) to generate a set of joints, a set of limbs, and a pose estimation for each subject from multiple subjects in an image 510 recorded by a camera. The multiple subjects can be, for example, performing rehabilitation exercises. In some implementations, multiple pose estimations 520 can overlaid with the image 510 of the multiple subjects to generate an overlaid image 530.

Figure 6:
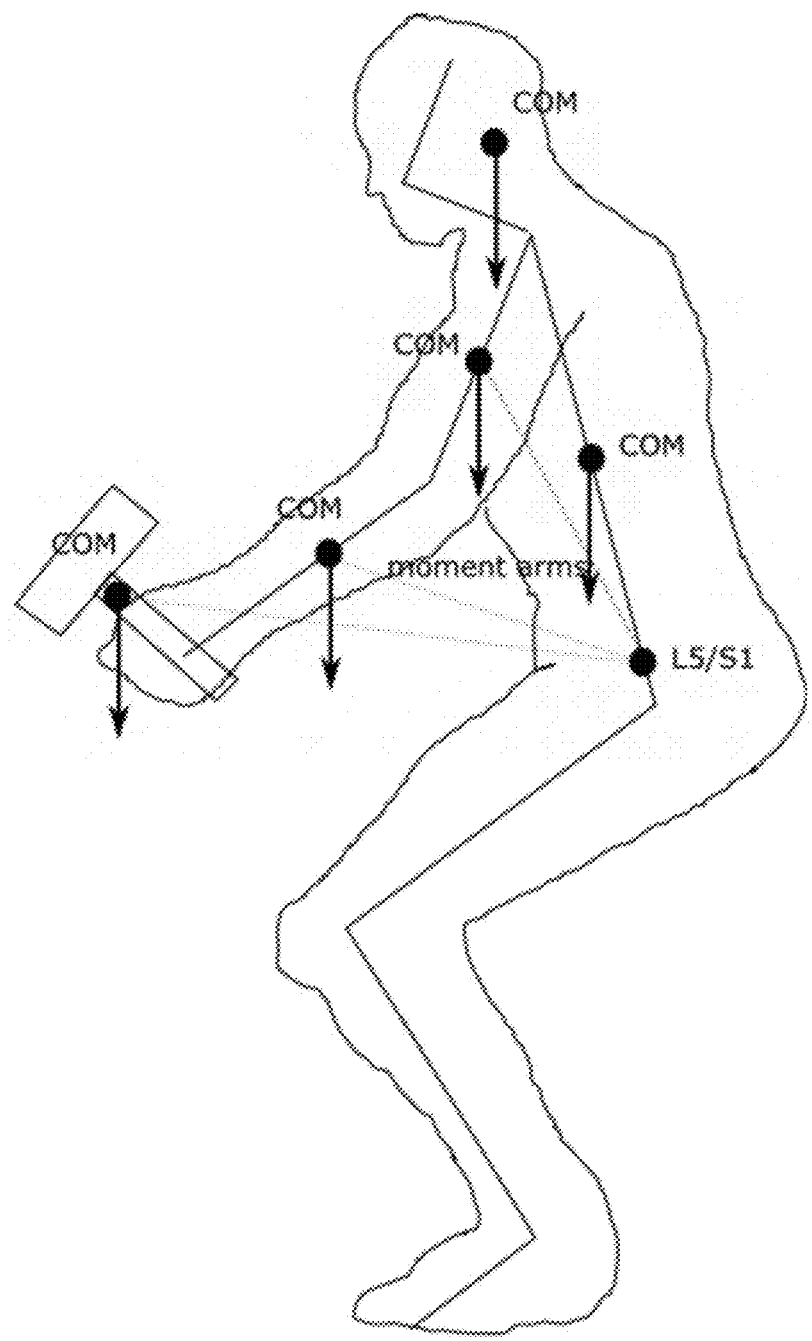
FIG. 6 is a schematic illustration of a method for determining a static load on a back joint, according to an embodiment.

FIG. 6 is a schematic illustration of a method for determining a static load on a back joint, according to an embodiment. A joint torque can refer to a total torque delivered around a joint, usually delivered by muscles. For each joint from a set of joint in a body of a subject (e.g., a patient, a worker, an athlete, etc.), multiple body parts can often contribute to a torque of force about the joint. The sum of all such torques can yield a total joint torque, which can be viewed as a rotational force about the joint. As shown in FIG. 6, a dynamic load model for the back joint (L5/S1 joint) can be computed by a method as described herein. The method, however, can be similarly applied to any of the other joints of the subject. A total dynamic load on the back joint can be the sum of the torques caused by weight, linear acceleration, and angular acceleration of the body segments above the L5/S1 joint.

A weighted torque of the L5/S1 joint can be computed by a sum of all weighted torques of body parts and objects weighted above the back. Those can include the head, the torso, the arms, the hands, or an object(s) in the hands. The weighted torque of a body part can be given by:

$$W = m \times g \times r$$

where m is the mass value of the body part or the object(s), g is the gravitational constant, and r the distance between the center of mass (COM) of the segment and the L5/S1 in the horizontal plane. The COM, the percentage of total body weight, and the radius of gyration for each body part or the object(s) can be modeled, for example, after data sets obtained from exact calculations made on cadaver bodies. The subjects' total mass may be given by the user or can be estimated using a 3D representation of a skeleton (as described with respect to FIG. 1) in conjunction with an auxiliary neural network that can predict the subject's Body Mass Index (MBI) and/or weight based on facial features of the subject and/or the 3D representation of the skeleton.

A total linear inertial torque is the sum of linear inertial torques of all body parts and any auxiliary objects interacting with the joint of interest (L5/S1 joint). The 3D reconstruction is formatted so that the vertical direction contains all information used to compute the linear force due to movement. The linear inertial torque can be computed using:

$$L = r \times m \times a_z$$

where r is the torque arm, m is the mass value of the body part or object, and $a_z$ denotes a vertical acceleration of the COM of a body part (e.g. head, torso, arms, hands, or object in the hands). The linear inertial torque can be computed for each image/frame from the 3D representation of the skeleton using a central difference method of differentiation. The linear inertial torque can be filtered to remove noise without changing characteristics of the image/frame using a double pass Butterworth filter whose cutoff frequency is obtained by applying Jackson's algorithm described above.

A total angular inertial torque is the sum of the angular inertial torques of all body parts and any auxiliary objects interacting with the back. The angular inertial torque for each body part can be computed using:

$$A = m \times \rho^2 \times \alpha$$

where m is a mass of the body part, ρ is a radius of gyration, and α is an angular acceleration. The angle of interest here is the segment angle between the body part and the transverse plane. The acceleration of this angle can be computed and filtered using the same techniques described above for the linear inertial torque. Finally, the total torque about the joint of interest (L5/S1 joint) can be computed as:

$$T=W+L+A$$

Setting all acceleration equal to zero in the above equations, can yield the static torque.

FIG. 7 is a schematic illustration of a classification model for classifying static pose data and dynamic pose data into risk injury categories, according to an embodiment. The classification model can classify static pose and/or dynamic pose data (as described with respect to FIG. 1) into predefined risk injury categories, and therefore, predict a likelihood for occurrence of an injury(ies). In one example, the classification model can be an XGBoost model that includes a set of hyper-parameters such as, for example, a number of boost rounds that defines the number of boosting rounds or trees in the XGBoost model, and/or maximum depth that defines a maximum number of permitted nodes from a root of a tree of the XGBoost model to a leaf of the tree. The XGBoost model can include a set of trees, a set of nodes, a set of weights, a set of biases, and/or the like.

Figure 8:
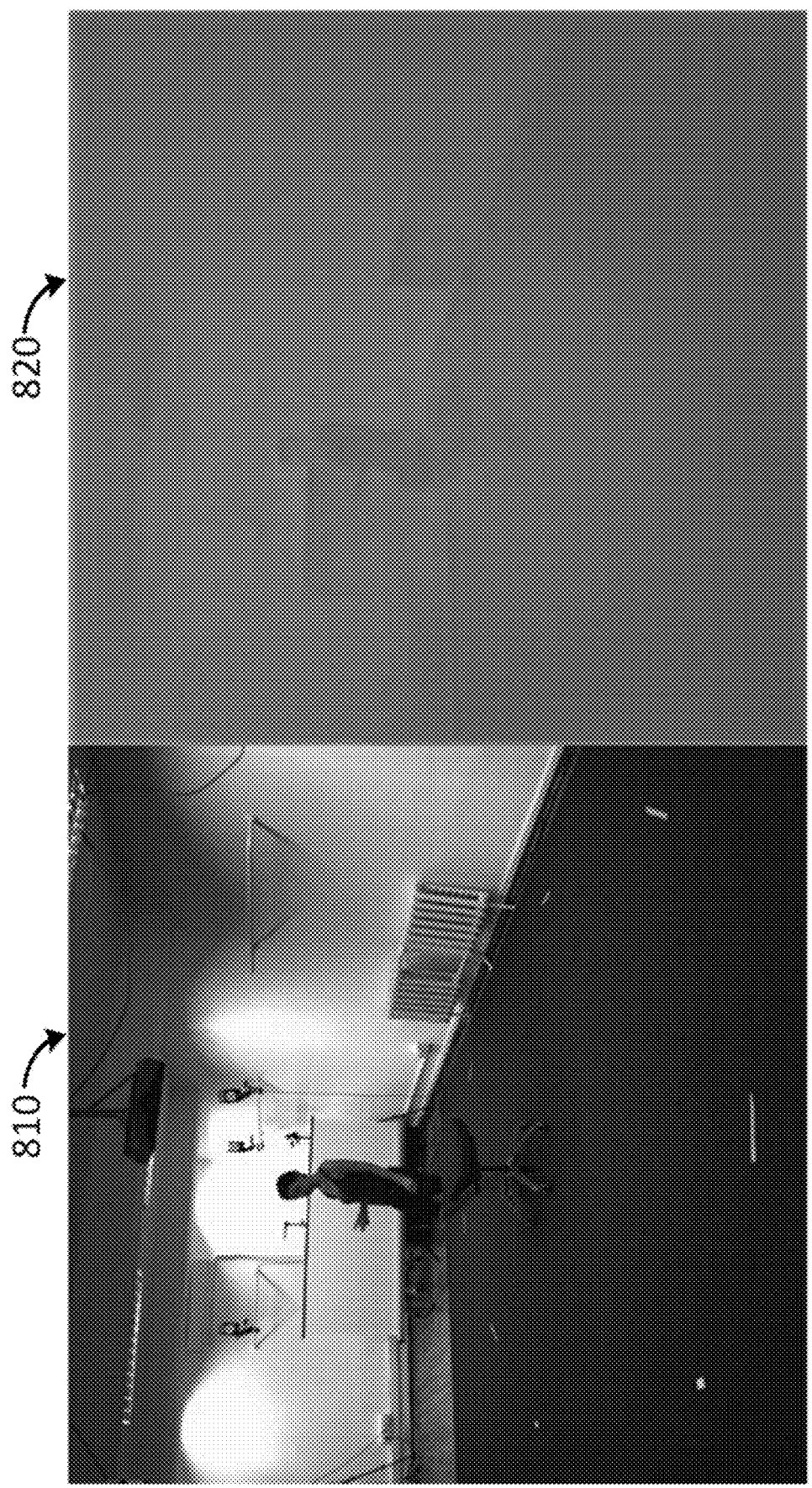
FIG. 8 is a schematic illustration of a method for a monocular image generation, according to an embodiment.

FIG. 8 is a schematic illustration of a method for a monocular image generation, according to an embodiment. A monocular depth estimation model (similar to the monocular depth estimation model described with respect to FIG. 1) can be used to encode a distance of a subject (e.g., a patient) relative to a focal center of a camera taking a set of images from the subject. The monocular depth estimation model can receive an image 810 (e.g., in red-green-blue (RGB) color coding) from the set of images to generate a monocular image 820. In some instances, the monocular image can be down-sampled by a factor of two. In some instances, the monocular depth estimation network can be an autoencoder neural network model with convolutional filters. In some implementations, the monocular depth estimation model can be configured generate a depth/distance value (as output of the monocular depth estimation model) from the image 810 (as input of the monocular depth estimation model).

It should be understood that the disclosed embodiments are not representative of all claimed innovations. As such, certain aspects of the disclosure have not been discussed herein. That alternate embodiments may not have been presented for a specific portion of the innovations or that further undescribed alternate embodiments may be available for a portion is not to be considered a disclaimer of those alternate embodiments. Thus, it is to be understood that other embodiments can be utilized, and functional, logical, operational, organizational, structural and/or topological modifications may be made without departing from the scope of the disclosure. As such, all examples and/or embodiments are deemed to be non-limiting throughout this disclosure.

Some embodiments described herein relate to methods. It should be understood that such methods can be computer implemented methods (e.g., instructions stored in memory and executed on processors). Where methods described above indicate certain events occurring in certain order, the ordering of certain events can be modified. Additionally, certain of the events can be performed repeatedly, concurrently in a parallel process when possible, as well as performed sequentially as described above. Furthermore, certain embodiments can omit one or more described events.

All definitions, as defined and used herein, should be understood to control over dictionary definitions, definitions in documents incorporated by reference, and/or ordinary meanings of the defined terms.

Some embodiments described herein relate to a computer storage product with a non-transitory computer-readable medium (also can be referred to as a non-transitory processor-readable medium) having instructions or computer code thereon for performing various computer-implemented operations. The computer-readable medium (or processor-readable medium) is non-transitory in the sense that it does not include transitory propagating signals per se (e.g., a propagating electromagnetic wave carrying information on a transmission medium such as space or a cable). The media and computer code (also can be referred to as code) may be those designed and constructed for the specific purpose or purposes. Examples of non-transitory computer-readable media include, but are not limited to, magnetic storage media such as hard disks, floppy disks, and magnetic tape; optical storage media such as Compact Disc/Digital Video Discs (CD/DVDs), Compact Disc-Read Only Memories (CD-ROMs), and holographic devices; magneto-optical storage media such as optical disks; carrier wave signal processing modules; and hardware devices that are specially configured to store and execute program code, such as Application-Specific Integrated Circuits (ASICs), Programmable Logic Devices (PLDs), Read-Only Memory (ROM) and Random-Access Memory (RAM) devices. Other embodiments described herein relate to a computer program product, which can include, for example, the instructions and/or computer code discussed herein.

Some embodiments and/or methods described herein can be performed by software (executed on hardware), hardware, or a combination thereof. Hardware modules may include, for example, a general-purpose processor, a field programmable gate array (FPGA), and/or an application specific integrated circuit (ASIC). Software modules (executed on hardware) can be expressed in a variety of software languages (e.g., computer code), including C, C++, Java™, Ruby, Visual Basic™, and/or other object-oriented, procedural, or other programming language and development tools. Examples of computer code include, but are not limited to, micro-code or micro-instructions, machine instructions, such as produced by a compiler, code used to produce a web service, and files containing higher-level instructions that are executed by a computer using an interpreter. For example, embodiments can be implemented using Python, Java, JavaScript, C++, and/or other programming languages and software development tools. For example, embodiments may be implemented using imperative programming languages (e.g., C, Fortran, etc.), functional programming languages (Haskell, Erlang, etc.), logical programming languages (e.g., Prolog), object-oriented programming languages (e.g., Java, C++, etc.) or other suitable programming languages and/or development tools. Additional examples of computer code include, but are not limited to, control signals, encrypted code, and compressed code.

The drawings primarily are for illustrative purposes and are not intended to limit the scope of the subject matter described herein. The drawings are not necessarily to scale; in some instances, various aspects of the subject matter disclosed herein can be shown exaggerated or enlarged in the drawings to facilitate an understanding of different features. In the drawings, like reference characters generally refer to like features (e.g., functionally similar and/or structurally similar elements).

The acts performed as part of a disclosed method(s) can be ordered in any suitable way. Accordingly, embodiments can be constructed in which processes or steps are executed in an order different than illustrated, which can include performing some steps or processes simultaneously, even though shown as sequential acts in illustrative embodiments. Put differently, it is to be understood that such features may not necessarily be limited to a particular order of execution, but rather, any number of threads, processes, services, servers, and/or the like that may execute serially, asynchronously, concurrently, in parallel, simultaneously, synchronously, and/or the like in a manner consistent with the disclosure. As such, some of these features may be mutually contradictory, in that they cannot be simultaneously present in a single embodiment. Similarly, some features are applicable to one aspect of the innovations, and inapplicable to others.

Where a range of values is provided, it is understood that each intervening value, to the tenth of the unit of the lower limit unless the context clearly dictates otherwise, between the upper and lower limit of that range and any other stated or intervening value in that stated range is encompassed within the disclosure. That the upper and lower limits of these smaller ranges can independently be included in the smaller ranges is also encompassed within the disclosure, subject to any specifically excluded limit in the stated range. Where the stated range includes one or both of the limits, ranges excluding either or both of those included limits are also included in the disclosure.

The phrase "and/or," as used herein in the specification and in the embodiments, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements can optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the embodiments, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the embodiments, "consisting of," will refer to the inclusion of exactly one element of a number or list of elements. In general, the term "or" as used herein shall only be interpreted as indicating exclusive alternatives (i.e., "one or the other but not both") when preceded by terms of exclusivity, such as "either," "one of," "only one of," or "exactly one of." "Consisting essentially of," when used in the embodiments, shall have its ordinary meaning as used in the field of patent law.

As used herein in the specification and in the embodiments, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements can optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the embodiments, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. A method, comprising:
receiving (1) a plurality of images of at least one subject and (2) at least one total mass value for the at least one subject,
executing a first machine learning model to identify a plurality of joints of the at least one subject from the plurality of images;
executing a second machine learning model to determine a plurality of limbs of the at least one subject based on the plurality of joints and the plurality of images;
generating a plurality of three-dimensional (3D) representations of a skeleton based on the plurality of joints and the plurality of limbs;
determining a mass value and a torque inertia value for each limb from the plurality of limbs, based on the at least one total mass value for the at least one subject and the plurality of 3D representations of the skeleton;
performing numerical differentiation on the plurality of 3D representations of the skeleton to produce a linear acceleration value and an angular acceleration value for each limb from the plurality of limbs;
determining a torque value for each limb from the plurality of limbs, based on at least one of the mass value and the linear acceleration value, or the torque inertia and the angular acceleration value, to generate a plurality of torque values; and
generating a risk assessment report based on at least one torque value from the plurality of torque values, being above a predetermined threshold.

2. The method of claim 1, further comprising:
executing, before executing the first machine learning model, a third machine learning model to generate a plurality of bounding boxes around the at least one subject based in the plurality of images, the plurality of images being ordered in a time sequence;
placing a plurality of trackers in a bounding box of a first image in the time sequence of the plurality of images, the first image being earlier in time than each remaining image from the plurality of images; and
executing a Kalman filter to track the plurality of trackers to identify the at least one subject across the plurality of images.

3. The method of claim 1, further comprising:
executing a Hungarian maximum matching algorithm to determine a plurality of relationships between the plurality of joints at each image from the plurality of images;
producing at least one skeleton for the at least one subject based on the plurality of joints and the plurality of relationships, for each image from the plurality of images; and
executing the second machine learning model to generate the plurality of 3D representations of the skeleton.

4. The method of claim 1, further comprising:
applying at least one filter to the plurality of 3D representations of the skeleton to at least one pose, the at least one filter being determined based on a frame rate used for recording the plurality of images; and
denoising the plurality of 3D representations of the skeleton based on the at least one pose to produce a plurality of refined 3D representations of the skeleton.

5. The method of claim 4, wherein the at least one filter includes at least one of a Butterworth filter, a final median filter, or a Savgol filter.

6. The method of claim 1, wherein the plurality of images was recorded by a camera having a focal point, the method further comprising:
executing, after executing the second machine learning model, a third machine learning model to generate at least one distance of the at least one subject relative to the focal point, based on the plurality of images;
generating the at least one pose based on the at least one distance and the plurality of 3D representations of the skeleton; and
denoising the plurality of 3D representations of the skeleton based on the at least one pose to produce a plurality of refined 3D representations of the skeleton.

7. The method of claim 6, wherein the third machine learning model is an autoencoder neural network model.

8. The method of claim 1, wherein the plurality of 3D representations of the skeleton are a first plurality of 3D representation of the skeleton, each 3D representation of skeleton from the first plurality of 3D representation of the skeleton being a Cartesian coordinate matrix, the method further comprising:
transforming the first plurality of 3D representations of the skeleton using at least one Euclidean matrix to produce a second plurality of 3D representations of the skeleton, each 3D representation from the second plurality of 3D representations of the skeleton being a Euler-angle representation; and
performing numerical differentiation on the second plurality of 3D representations of the skeleton to produce a plurality of time sequences of joint movement velocity values.

9. The method of claim 8, further comprising:
determining a plurality of joint angles based on the plurality of joints in the first plurality of 3D representations of the skeleton; and
determining a plurality of maximum torque values based on the plurality of time sequences of joint movement velocity values and the plurality of joint angles.

10. The method of claim 9, further comprising:
determining a plurality of time durations of a plurality of activities of the plurality of joints based on the plurality of time sequences of joint movement velocity values; and
determining a plurality of total limit values for each joint from the plurality of joints based on the plurality of maximum torque values and the plurality of time durations for the plurality of activities.

11. The method of claim 1, wherein the at least one subject is not wearing any motion sensors.

12. The method of claim 1, further comprising:
determining a center of mass position from a plurality of center of mass positions for each limb from the plurality of limbs of the at least one subject based on the plurality of 3D representations of the skeleton.

13. The method of claim 1, further comprising:
determining the torque value for each limb from the plurality of limbs, based on a weight value, a torque arm value, the mass value, the linear acceleration value, the torque inertia, and the angular acceleration value.

14. A non-transitory processor-readable medium storing code representing instructions to be executed by a processor, the code comprising code to cause the processor to:
execute a first machine learning model to identify a plurality of joints of at least one subject for each image from a plurality of images of the at least one subject performing a plurality of activities;
execute a second machine learning model to determine a plurality of limbs of the at least one subject to generate a first plurality of three-dimensional (3D) representations of a skeleton based on the plurality of images;
transform the first plurality of 3D representations of the skeleton to produce a second plurality of 3D representations of the skeleton, each 3D representation from the second plurality of 3D representations of the skeleton being a Euler-angle representation;
perform numerical differentiation on the second plurality of 3D representations of the skeleton to produce a plurality of time sequences of joint movement velocity values;
determine a plurality of maximum torque values based on the plurality of time sequences of joint movement velocity values and a plurality of joint angles that are determined based on the plurality of joints in the first plurality of 3D representations of the skeleton; and
determine a plurality of total limit values for each joint from the plurality of joints based on the plurality of maximum torque values and a plurality of time durations for the plurality of activities.

15. The non-transitory processor-readable medium of claim 14, wherein the first plurality of 3D representations is transformed by an Euler-angle representation to generate the second plurality of 3D representations.

16. The non-transitory processor-readable medium of claim 14, the code further comprising code to cause the processor to:
execute, before executing the first machine learning model, a third machine learning model to generate a plurality of bounding boxes around the at least one subject based on the plurality of images, the plurality of images being ordered in a time sequence;
place a plurality of trackers in a bounding box of a first image in the time sequence of the plurality of images, the first image being earlier in time than each remaining image from the plurality of images; and execute a Kalman filter to track the plurality of trackers to identify the at least one subject across the plurality of images.

17. The non-transitory processor-readable medium of claim 14, the code further comprising code to cause the processor to:

execute a Hungarian maximum matching algorithm to determine a plurality of relationships between the plurality of joints at each image from the plurality of images;

produce at least one skeleton for the at least one subject based on the plurality of joints and the plurality of relationships, for each image from the plurality of images; and execute the second machine learning model to generate the first plurality of 3D representations of the skeleton.

18. The non-transitory processor-readable medium of claim 14, the code further comprising code to cause the processor to:

apply at least one filter to the first plurality of 3D representations of the skeleton to generate at least one pose, the at least one filter being determined based on a frame rate used for recording the plurality of images; and denoise the first plurality of 3D representations of the skeleton based on the at least one pose to produce a plurality of refined 3D representations of the skeleton.

19. An apparatus, comprising:

a camera configured to capture a plurality of images of at least one subject, at a frame rate;

a memory operatively coupled to the camera, the memory configured to store the plurality of images; and a processor operatively coupled to the memory, the processor configured to:

execute a first machine learning model to identify a plurality of joints of the at least one subject based on the plurality of images;

execute a second machine learning model to determine a plurality of limbs of the at least one subject based on the plurality of images;

generate a plurality of three-dimensional (3D) representations of a skeleton based on the plurality of joints and the plurality of limbs;

apply at least one filter to the plurality of 3D representations of the skeleton to generate a plurality of poses, the at least one filter being determined based on the frame rate;

determine a plurality of joint angles based on the plurality of joints in the plurality of 3D representations of the skeleton;

execute a statistical model to generate statistical data based on the plurality of joint angles and the plurality of poses; and execute a third machine learning model to predict a likelihood of occurrence of at least one injury based on the plurality of poses and the statistical data.

20. The apparatus of claim 19, wherein the statistical data include at least one of a plurality of mean values for joint angles, a plurality of variance values for joint angles, a plurality of mean poses, or a plurality of variance poses.

21. The apparatus of claim 19, wherein the processor is further configured to:

execute, before executing the first machine learning model, a fourth machine learning model to generate a plurality of bounding boxes around the at least one subject based in the plurality of images, the plurality of images being ordered in a time sequence;

place a plurality of trackers in a bounding box of a first image in the time sequence of the plurality of images, the first image being earlier in time than each remaining image from the plurality of images; and execute a Kalman filter to track the plurality of trackers to identify the at least one subject across the plurality of images.

22. The apparatus of claim 19, wherein the camera has a focal point, the processor further configured to:

execute, after executing the second machine learning model, a fourth machine learning model to generate at least one distance of the at least one subject relative to the focal point, based on the plurality of images;

generate the at least one pose based on the at least one distance and the plurality of 3D representations of the skeleton; and denoise the plurality of 3D representations of the skeleton based on the at least one pose to produce a plurality of refined 3D representations of the skeleton.

23. The apparatus of claim 19, wherein the third machine learning model is an eXtreme Gradient Boosting (XGBoost) model.

24. The apparatus of claim 19, wherein the third machine learning model is configured to classify the plurality of poses of the at least one subject to at least one predetermined injury category to generate the likelihood of occurrence of the at least one injury.

* * * * *